United States Patent [19]

Pascal et al.

[11] 4,288,638
[45] * Sep. 8, 1981

[54] PROCESS FOR THE SYNTHESIS OF 2,4-DINITRO-6-T-BUTYL-3-METHYLANISOLE, REFERRED TO AS MUSK AMBRETTE

[75] Inventors: Hélène M. Pascal, Le Pontet; Jean-Marie L. Emeury, Sorgues, both of France

[73] Assignee: Societe Nationale des Poudres et Explosifs, Paris, France

[*] Notice: The portion of the term of this patent subsequent to Nov. 25, 1997, has been disclaimed.

[21] Appl. No.: 122,476

[22] Filed: Feb. 19, 1980

Related U.S. Application Data

[62] Division of Ser. No. 970,139, Dec. 18, 1978, Pat. No. 4,236,029.

[30] Foreign Application Priority Data

Dec. 29, 1977 [FR] France .................. 77 39625

[51] Int. Cl.³ .............................................. C07C 41/18
[52] U.S. Cl. ..................................................... 568/584
[58] Field of Search ......................................... 568/584

[56] References Cited

U.S. PATENT DOCUMENTS

| | | | |
|---|---|---|---|
| 2,007,234 | 7/1935 | Wirth | 568/584 |
| 2,007,241 | 7/1935 | Dahlen et al. | 568/584 |
| 2,038,620 | 4/1936 | Weiland et al. | 568/584 |
| 2,493,797 | 1/1950 | Wood | 568/584 |

OTHER PUBLICATIONS

Carpenter et al., Jour. Org. Chem., vol. 16 (1951), pp. 586–620.

*Primary Examiner*—Bernard Helfin
*Attorney, Agent, or Firm*—Bucknam and Archer

[57] ABSTRACT

The invention relates to a process for the synthesis of 2,4-dinitro-6-t-butyl-3-methylanisole or musk ambrette.

The process according to the invention is characterized in that 6-t-butyl-3-methylanisole is reacted with a nitrating mixture consisting of 30 to 50% of acetic acid, 20 to 30% of acetic anhydride and 25 to 45% by weight of nitric acid, at between 7° and 15° C. The product is recovered in the pure state with a good yield by adding small amounts of water to the crude reaction mixture.

Application: Synthesis of a scented product.

4 Claims, No Drawings

PROCESS FOR THE SYNTHESIS OF 2,4-DINITRO-6-T-BUTYL-3-METHYLANISOLE, REFERRED TO AS MUSK AMBRETTE

This is a division of application Ser. No. 970,139 filed Dec. 18, 1978 and now U.S. Pat. No. 4,236,029.

The present invention relates to a process for the preparation of 2,4-dinitro-6-tert.-butyl-3-methylanisole.

2,4-Dinitro-6-t-butyl-3-methylanisole is better known by the name Musk Ambrette and is widely used as a scent. By virtue of the fact that, in this latter respect, it is of greater value than homologous compounds, this product is in particularly high demand.

Several processes for the manufacture of Musk Ambrette were proposed a relatively long time ago. TCHICHIBABINE, in the Bulletin de la Societe Chimique de France of 1939, volume 4, page 439, recommended starting from 3-methyl-6-t-butylphenol and successively nitrating it (using nitric acid) and methylating the phenol group (using dimethyl sulphate) in accordance with equations (I) and (II) below:

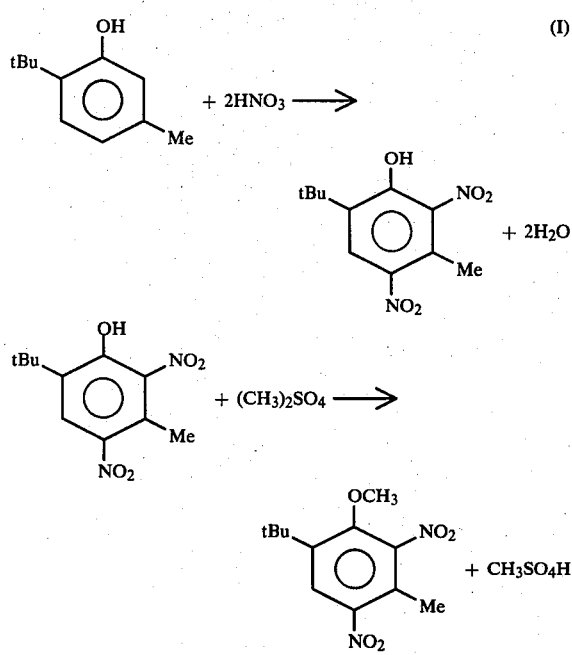

However, this is not an industrial process because the reactions take place with difficulty and give rise to a mixture of isomers or of homologues.

CARPENTER, EASTER and WOOD, in volume 16, No. 4, pages 586–617 of the Journal of Organic Chemistry of 1951, proposed to nitrate 3-methyl-6-t-butylanisole, at between −10° and +20° C., using a mixture of 98% strength nitric acid (5 mols) and acetic anhydride (3.5 mols). However, although this process indeed makes it possible to obtain Musk Ambrette with fairly good yields, it requires, on the other hand, the use of a nitrating mixture which is very rich in nitric acid (about 50%) in order for total nitration to be achieved. In fact, this process requires the use of temperatures well below normal temperature, generally substantially below 0° C. and preferably in the region of −15° C.

However, despite these rather restrictive conditions, it is not possible to obtain a product of satisfactory purity directly in the crude reaction mixture, as proved by the works of S. ABE which appeared in volume 21, No. 12, pages 936–940 of Yuki Gosci Kayaku Kyokai Shi of 1963 (Chemical Abstracts 60:4038a). In fact, it is not possible to avoid the production of quinone derivatives and especially the removal of the tert.-butyl group from the molecule.

Finally, it has been proposed to avoid the temperature constraints by using a special apparatus for continuous nitration. This apparatus, described by Gel'Perin et al. in Zhur. Vsesojuz Khim. Obshchestra im. D.I. Mendeleeva (1960), 5, pages 438–442, requires a large investment which increases the production costs to a prohibitive degree. Furthermore, this process does not make it possible to resolve the difficulty of the separation and purification of the product formed.

A common feature of the former processes is that the reaction mixture is finally poured onto ice or cold water in order to separate out the organic phase and wash the nitrated product. The latter is then generally taken up in an organic solvent and subsequently re-washed until neutral, after which the organic solvent is evaporated off and the Musk Ambrette is recrystallised. It is clear that these essential operations increase the cost price of the Musk Ambrette obtained by the former processes.

The Applicant Company has now discovered a process for the manufacture of Musk Ambrette, which makes it possible to use a nitrating mixture containing relatively little nitric acid and an easily accessible temperature. This process additionally makes it possible to recover Musk Ambrette of satisfactory purity particularly easily, the overall yield of the process being at least equal to the yields of the older processes.

The process according to the invention fundamentally consists in treating 3-methyl-6-t-butylanisole with a ternary nitrating mixture comprising acetic anhydride, nitric acid and acetic acid, at a temperature between +5° and +30° C. and preferably between 7° and 15° C.

According to a preferred variant of the process according to the invention, the nitrating mixture used initially comprises a total of 30 to 50% by weight of acetic acid, 20 to 30% by weight of acetic anhydride and 25 to 45% by weight of nitric acid.

The terms acetic acid and nitric acid are to be understood as meaning concentrated acids of the usual technical purity, that is to say acids containing at least 97% by weight of $CH_3COOH$ and $HNO_3$ respectively. Of course, it is also possible to prepare the mixture according to the invention by using less acetic acid, more acetic anhydride and an aqueous solution of nitric acid of, for example, 70% strength. However, this is of less value.

The process according to the invention can be applied for nitrating ratios of between 5 and 6, the nitrating ratio being the ratio of the mass of nitrating mixture to the mass of substance to be nitrated. Thus, it is possible to use from 3.5 to 7.5 mols, and preferably from 4.5 to 5.5 mols, of nitric acid per mol of t-butyl-methylanisole to be nitrated.

In accordance with the process according to the invention, it has been found advantageous first to prepare a sediment comprising the nitrating mixture or only some of the constituents of this mixture, and then to introduce the t-butyl-methylanisole, pure or in solution, and, if necessary, the remainder of the constituents of the nitrating mixture. For example, the butylmethylanisole can be in solution in acetic anhydride.

According to a particularly preferred variant, t-butyl-methylanisole is introduced, at the same time as all or part of the nitric acid, onto a sediment mixture consisting of acetic acid, acetic anhydride and, if necessary, the remainder of the nitric acid.

As the reaction is violently exothermic, the t-butyl-methylanisole must be introduced gradually, with the result that the reaction time largely depends on the amounts of reactants employed. In general, however, the reaction conditions defined in the present process make it possible to complete the introduction, which is preferably slow at the start, within a period of between 20 minutes and 2 hours, the reactor being cooled in a simple manner using brine.

When the introduction is complete, the reaction is already very advanced, but the stage in which all the reactants are brought into contact should be followed by a stage for completion of the reaction, which consists in leaving the reaction mixture for 20 to 90 minutes at ambient temperature (about 25° C.), whilst stirring moderately (the medium is homogeneous).

The Musk Ambrette can be recovered either by precipitating the crude reaction mixture obtained after the completion stage onto a mixture of water and ice, in a manner which is in itself known, or by introducing into the said mixture, preferably slowly and whilst stirring, one or more amounts of water which are small compared with those employed in the preceding method and less than 100% by weight of the amount of nitrating mixture used. In the first case, it is necessary to take up the product in an organic solvent such as benzene or, preferably, hexane. In the second case, it has been discovered that the Musk Ambrette precipitates with an astonishing yield and purity.

In particular, if a first amount of water is introduced which represents from about 5 to 40% by weight of the nitrating mixture involved in the reaction, a first precipitate of Musk Ambrette of excellent purity is obtained (sharp melting point between 83° and 85° C. and generally about 84° C.) with a yield of 40 to 65%, relative to the t-butyl-methylanisole. By adding, in the same manner, one or more additional small amounts of water, each representing from 1 to 15% by weight of the initial nitrating mixture, further amounts of Musk Ambrette of deteriorating grade, which can nevertheless be suitable for most industrial applications, are precipitated and collected between each addition.

According to another variant, an amount of water representing, by weight, from 25% to 100% of the weight of the nitrating mixture used is introduced all at once into the crude reaction mixture. This then gives a precipitate of pure Musk Ambrette (melting point above 83° C.) with a yield of 55 to 70%.

In each case, it is possible to further improve the purity of the recovered products by means of a clearing operation using an ice-cooled alcohol, for example methanol or isopropanol. Furthermore, it has been found advantageous to cool the crude synthesis mixture slightly to a temperature which is preferably between 15° and 20° C., before introducing the water and therefore carrying out the precipitation. In order to complete this precipitation, it is also advantageous to stir the medium moderately for 15 to 45 minutes.

Finally, it can be considered that, when 100 to 200% by weight of water, relative to the nitrating mixture involved in the synthesis, has been introduced into the reaction medium, all the Musk Ambrette of marketable purity, which is produced by the process according to the invention and separated by fractional precipitation, has been recovered; the yield of the synthesis is 60 to 85%, depending on the desired degree of purity of the Musk Ambrette.

The process according to the invention uses much milder conditions than the processes of the prior art. It is completely surprising that a better purity and yield are obtained under these conditions.

Furthermore, it must be appreciated that $HNO_3$/acetic anhydride mixtures must be handled with great precautions, because it has been shown that such mixtures can explode. The invention therefore represents a distinct advance both from the technical point of view (less harsh nitrating bath, improved yield, purity and recovery and lower reaction temperature) and from the point of view of safety.

Further advantages of the invention will become apparent in the following examples which must not be considered as limiting the invention.

EXAMPLE 1

A kilogram of a sediment consisting of 40% of acetic acid, 28% of acetic anhydride and 32% of 98% strength nitric acid was prepared.

The temperature of the medium was kept at 25° C., using a brine bath, and 178 g of 6-t-butyl-3-methylanisole were run into this nitrating bath in the course of 1 hour, whilst stirring.

Once the introduction was complete, the reaction medium was kept at 25° C. for half an hour. The mixture obtained was then poured onto a mixture of water and ice. The organic phase was taken up in 1,500 ml of hexane and, after evaporating off the solvent, 262 g of a product having a melting point of 64° C. and containing 80% of Musk Ambrette were collected. The yield of this product is therefore 76%.

EXAMPLE 2

178 g of 3-methyl-6-t-butylanisole and 330 g of 98% strength nitric acid were run simultaneously, in the course of one hour, into 670 g of a sediment consisting of 52% of acetic acid and 48% of acetic anhydride, keeping the temperature at 25° C. and whilst stirring the medium.

After having left the mixture to stand for 30 minutes at 25° C., it was poured onto ice and 240 g of product, containing 88% of Musk Ambrette and having a melting point of 64° C., were collected by taking up the mixture in 1,500 ml of hexane. The yield of pure Musk Ambrette from the reaction is 78%.

EXAMPLE 3

17.8 g of 3-methyl-6-t-butylanisole and 16 g of nitric acid (98% strength) were introduced, in the course of one hour, into 84 g of a sediment consisting of 49% of acetic acid, 31% of acetic anhydride and 20% of nitric acid, keeping the temperature of the medium at 10° C.

After having stirred the medium moderately for one hour at 25° C., 22 ml of water were introduced into the said medium and 11.5 g of Musk Ambrette, which had precipitated, were collected. This product had a melting point of 84° C. and represented 43% of the theoretical yield.

30 ml of water were then introduced into the medium and 7.8 g of Musk having a melting point of 74° C. were precipitated.

By adding 200 ml of water, a further 3.2 g of a product containing about 50% of Musk were collected.

Determination of the crude reaction product showed that it contained 71% of Musk.

EXAMPLE 4

The conditions of Example 3 were repeated, using amounts which were ten times greater.

Thus, 250 ml of water were introduced into the medium obtained. 140 g (52% of theory) of pure Musk Ambrette, having a melting point of 85° C., were collected.

A second addition of 100 ml of water made it possible to collect 58 g of Musk having a melting point of 73° C.

A third addition of 100 ml gave a further 12 g of product having a melting point of 72° C. and a last addition of 1,000 ml gave 24 g of product containing only 30% of Musk.

The crude yield of Musk from the reaction is 72%.

EXAMPLE 5

The conditions of Example 4 were repeated, but 300 ml of water were added all at once.

166 g of pure Musk Ambrette, having a melting point of 84° C., were collected with a yield of 62%, relative to the theoretical amount.

The medium was then immersed in one liter of water and 60 g of a precipitate of impure product containing 30% of Musk were collected.

EXAMPLE 6

If 330 ml of water are run into the crude reaction mixture obtained in Example 5, 185 g of Musk Ambrette, containing more than 99% of Musk and melting at 84° C., are collected. The yield of product of excellent purity is therefore 69%.

EXAMPLE 7

If 280 ml of water are run into the crude reaction mixture obtained in Example 5, which has been cooled to about 18° C., 162 g of very pure musk, melting at 85° C., are collected after having stirred the mixture for 30 minutes at 18° C. (yield 61%). If an additional 110 ml are run in, a further 65 g of 65% pure Musk, melting at 73° C., are collected.

If a further 110 ml are run in, 13 g of impure precipitate are recovered and, if the medium thus obtained is immersed, a further 27 g of product, containing 30% of musk and 70% of 4,6-dinitro-3-methylanisole, are recovered.

The overall yield of pure Musk Ambrette from the reaction is 81%, nearly three quarters of which has therefore been collected in the pure state.

We claim:

1. Process for the synthesis of 2,4-dinitro-6-t-butyl-3-methylanisole which consists of reacting 3-methyl-6-t-butylanisole with a ternary nitrating mixture which comprises acetic anhydride, acetic acid and nitric acid at between 5° and 30° C. wherein said nitrating mixture consists of a total of 30 to 50% by weight of acetic acid, 20 to 30% by weight of acetic anhydride and 25 to 45% by weight of nitric acid, and said 2,4-dinitro-6-t-butyl-3-methylanisole is recovered as a precipitate by introducing into the crude reaction mixture, preferably slowly and while stirring, one or more small amounts of water which are less than 100% by weight of the amount of nitrating mixture used.

2. Process according to claim 1, wherein an amount of water representing, by weight, from 25 to 100% of the weight of the nitrating mixture used is introduced all at once into the crude reaction mixture.

3. Process according to claim 1, wherein a first amount of water, representing from 5 to 40% by weight of the nitrating mixture used, is introduced and the precipitate of 2,4-dinitro-6-t-butyl-3-methylanisole obtained is collected, and one or more small amounts of water, each representing from 1 to 15% by weight of the nitrating mixture, are then introduced, additional amounts of said product of deteriorating grade are collected between each addition.

4. Process according to claim 1, wherein the temperature of the crude reaction mixture is brought to between 15° and 20° C. before the water is introduced.

* * * * *